(12) United States Patent
Lasky et al.

(10) Patent No.: US 6,190,334 B1
(45) Date of Patent: Feb. 20, 2001

(54) METHOD AND APPARATUS FOR THE IMAGING OF TISSUE

(75) Inventors: Harold J. Lasky, Evanston, IL (US); Kenneth A. Pasch, North Eastham, MA (US)

(73) Assignee: RBP, Inc., Chicago, IL (US)

( * ) Notice: Under 35 U.S.C. 154(b), the term of this patent shall be extended for 0 days.

(21) Appl. No.: 09/317,935

(22) Filed: May 24, 1999

(51) Int. Cl.$^7$ .................................................. A61B 5/00
(52) U.S. Cl. ............................................................ 600/587
(58) Field of Search .................................. 600/550, 552, 600/553, 587

(56) References Cited

U.S. PATENT DOCUMENTS

| | | | |
|---|---|---|---|
| 4,250,894 | 2/1981 | Frei et al. ............................. | 128/774 |
| 5,524,636 | 6/1996 | Sarvazyan et al. ................... | 128/774 |
| 5,785,663 | 7/1998 | Sarvazyan ............................. | 600/587 |
| 5,833,633 | 11/1998 | Sarvazyan ............................. | 600/587 |
| 5,833,634 | 11/1998 | Laird et al. ........................... | 600/587 |
| 5,836,894 | 11/1998 | Sarvazyan ............................. | 600/587 |
| 5,860,934 | 1/1999 | Sarvazyan ............................. | 600/587 |

*Primary Examiner*—Max Hindenburg
(74) *Attorney, Agent, or Firm*—Baker & McKenzie

(57) ABSTRACT

A tissue examination apparatus particularly useful for automated breast palpation is provided. The apparatus includes an actuator having an extendable probe for contacting the tissue and an electronic control module that controls extension and retraction of the probe. The electronic control module determines displacement distances of the probe and forces exerted on the probe at each displacement distance when the probe is extended so as to contact the tissue. The apparatus also has a drive assembly secured to a frame. The drive assembly includes a movable carriage and a corresponding drive motor. The actuator is mounted on the movable carriage. The drive motor receives motion control signals from the electronic control module and thereby moves the actuator over a patient's body. At different locations, the probe is extended into the patient's tissue and force and displacement readings are obtained and sent to the electronic control module. A signal processor such as a computer receives the force and the displacement distance determinations from the electronic control module and analyzes the force and the displacement distance determinations to provide a visual data analysis indicating any lesion within the tissue.

21 Claims, 8 Drawing Sheets

METHOD AND APPARATUS FOR THE IMAGING OF TISSUE

BACKGROUND OF THE INVENTION

1. Field of the Invention

The present invention relates to tissue examination. More particularly, the invention relates to an automated breast palpation device that provides images of palpable findings within breast tissue.

2. Description of the Related Art

Early detection of the formation of tumors or lesions, particularly those caused by cancer, has been a problem for some time, and numerous devices and techniques have been proposed or developed for cancer diagnosis. For example, mammography and physician examination are widely used techniques that have proven to be effective breast cancer diagnosis tools. A number of other technologies have also been proposed for breast cancer diagnosis such as thermography, ultrasound, CAT scanning and light scanning. In most situations, these technologies have proven to be ineffective. MRI is the latest development in breast cancer diagnosis and, as yet, the jury is still out on its ability to separate benign from malignant lesions. The high current cost of the MRI examination and the need for injected contrast media remove it from consideration for cancer screening. Even with continued research into new technologies for breast cancer diagnosis, mammography and physician examinations including breast palpation remain the standard examinations in breast cancer detection.

The preeminence of mammography and physician examinations in breast cancer detection can be seen in the American Cancer Society (ACS) guidelines for breast cancer detection shown in Table 1 below.

| ACS Guidelines for Cancer Detection | |
|---|---|
| Age | Recommendation |
| 20 | Breast Self Examination (BSE) monthly |
| 20–40 | Breast Physician Examination (PE) every 3 years |
| 40+ | Breast Physician Examination (PE) every year |
| 35–40 | Initial mammogram |
| 40–49 | Mammogram every 1–2 years |
| 50+ | Mammogram every year |

It can be seen that breast self examination (BSE) and physician examination (PE) are the only recommended detection methods prior to age 35 and except for an initial mammogram, until age 40. Physician examination (PE) additionally accompanies screening mammograms. However, even though a physician examination should accompany a mammogram, there are mammography facilities that do not provide the service. Not only does this necessitate a trip to a second facility, it entails a second appointment and additional cost. As a result, certain women may not undergo a breast physician examination in conjunction with a mammogram.

It is recognized that mammography and physician examination (PE) are synergistic techniques, i.e., a combination of these techniques increases the effectiveness of breast cancer detection. Certain physicians perform a breast physical examination (PE) on each woman receiving a mammogram. It has been observed that some women with initially negative physical findings and suspicious mammograms have some palpable finding on focused breast palpation. Ultrasound and biopsy have proven this relationship. Therefore, it is obvious that a physician examination including breast palpation is an accurate method of breast cancer detection.

However, breast palpation does have certain limitations. The challenge is to differentiate significant palpable findings from the nonsignificant ones that are little different. In many patients, the findings are not conclusive and the breast examiner has difficulty in interpreting what his fingers feel in the breast. The question that must be answered is "is the nodularity which he feels within the limits of the normal physiologic variation in breast structure or does it represent a dominant tumor due to inflammatory or neoplastic disease?" It is apparent that a measurable difference in resistance may exist between significant and nonsignificant findings. Unfortunately, the human fingertip may not be sensitive enough to measure the difference. In fact, it is believed that palpation is not able to detect tumors of less than about one centimeter in size.

Breast palpation also has data acquisition and analysis limitations not present in other breast cancer detection techniques. For instance, mammography provides the physician with a visual image that can be reviewed and compared and saved for future reference. This enables mammography to demonstrate a developing mass using serial studies. In contrast, manual breast palpation by its nature cannot provide a visual image for review and future reference.

In order to increase the sensitivity of palpation and allow for data acquisition and analysis, a number of devices for mimicking breast palpation to detect tumors have been developed. For example, U.S. Pat. No. 4,250,894 discloses an instrument for breast palpation that use a plurality of electret strips which are pressed into the body being examined by a pressure member which applies a stress to the tissue beneath the electret strips. A signal processor interrogates the output voltage of each of the strips and the output is displayed to produce a display characteristic that shows the presence of an inclusion in the breast tissue being examined. U.S. Pat. No. 5,833,634 discloses a tissue examination device that includes: (1) a transducer element for generating a signal in response to force imposed on the transducer element in accordance with the varying properties of the underlying tissue structure and (2) circuitry for detecting a variation in the signal as an indication of a localized area of stiffer tissue within the tissue. U.S. Pat. Nos. 5,524,636 & 5,860,934 disclose a device including a pressure sensor array, a data acquisition circuit and a microprocessor mounted in a hand held pad. Detection of any lumps in the breast is achieved by analyzing the features of the pressure pattern when the pad is pressed to the breast.

While these devices may be valuable tools for breast cancer detection, they do have certain limitations. Specifically, these devices are hand held and therefore, cannot be moved over the breast in a repeatable pattern that allows for accurate serial studies.

Therefore, there is a continuing need for improved breast palpation methods. Specifically, there is a need for an automated breast palpation machine that: (1) provides an image of palpable findings that can be reviewed; (2) provides an image of palpable findings that will be available to the mammographer at the time of interpretation; (3) includes repetitive examination that provides a means of detecting a developing locus of increased resistance before a recognizable palpable mass has appeared; and (4) provides the opportunity to detect significant palpable resistance that is presently below the threshold of clinical recognition.

It is therefore an object of the present invention to provide an automated breast palpation machine that generates an image that can be reviewed and compared to other images.

It is still another object of the present invention to provide an automated breast palpation machine that can recognize significant palpable findings currently below the clinical threshold of manual breast palpation.

It is yet another object of the present invention to provide an automated breast palpation machine that can demonstrate a developing mass on serial studies.

It is a further object of the present invention to provide an automated breast palpation machine that can insure that breast palpation is used in conjunction with screening mammograms.

SUMMARY OF THE INVENTION

The foregoing needs are satisfied and the foregoing objects achieved by a tissue examination apparatus that includes an actuator having an extendable probe for contacting the tissue and an electronic control module that controls extension and retraction of the probe. The electronic control module determines displacement distances of the probe and forces exerted on the probe at each displacement distance when the probe is extended so as to contact tissue. The apparatus also has a drive assembly secured to a frame. The drive assembly includes a movable carriage and a corresponding drive motor. The actuator is mounted on the movable carriage. The drive motor receives motion control signals from the electronic control module and thereby moves the actuator over a patient's body. At different locations, the probe is extended into the patient's tissue and force and displacement readings are obtained and sent to the electronic control module. A signal processor such as a computer receives the force and the displacement distance determinations from the electronic control module and analyzes the force and the displacement distance determinations to provide a visual data analysis indicating any lesion within the tissue.

The tissue examination apparatus of the present invention has many advantages, especially when used as an automated breast palpation device. For example, the apparatus improves breast physical examination procedure by producing a digitized record of the palpation. This provides the following advantages: (1) high-resolution tactile records can be converted to visual form for direct inspection thus providing a second perspective of examination, (2) records from periodic exams can be used as in serial mammography to detect trends that would otherwise go unnoticed, (3) the subjectivity of the person making the exam is eliminated by directly digitizing sensor readings, (4) a computer can easily handle the data generated from a fibrous breast that would normally overload the sensory and processing ability of the examiner, (5) tissue resistance can be measured with sufficient sensitivity to differentiate slight variation (5000 units), (6) areas of different resistance as small as 5 millimeters in diameter can be resolved, (7) color images in the form of a topographic map can be generated to indicate variations in resistance by color differences, (8) repeatable, accurate, positioning of the device relative to the breasts is possible so that images are comparable and variation in resistance at a given locus can be detected and flagged, and (9) computer comparison of the prior recorded image with the current image to determine variation is possible.

BRIEF DESCRIPTION OF THE DRAWINGS

These and other features, aspects, object and advantages of the present invention will become better understood upon consideration of the following detailed description, appended claims and accompanying drawings where:

Figure 1:
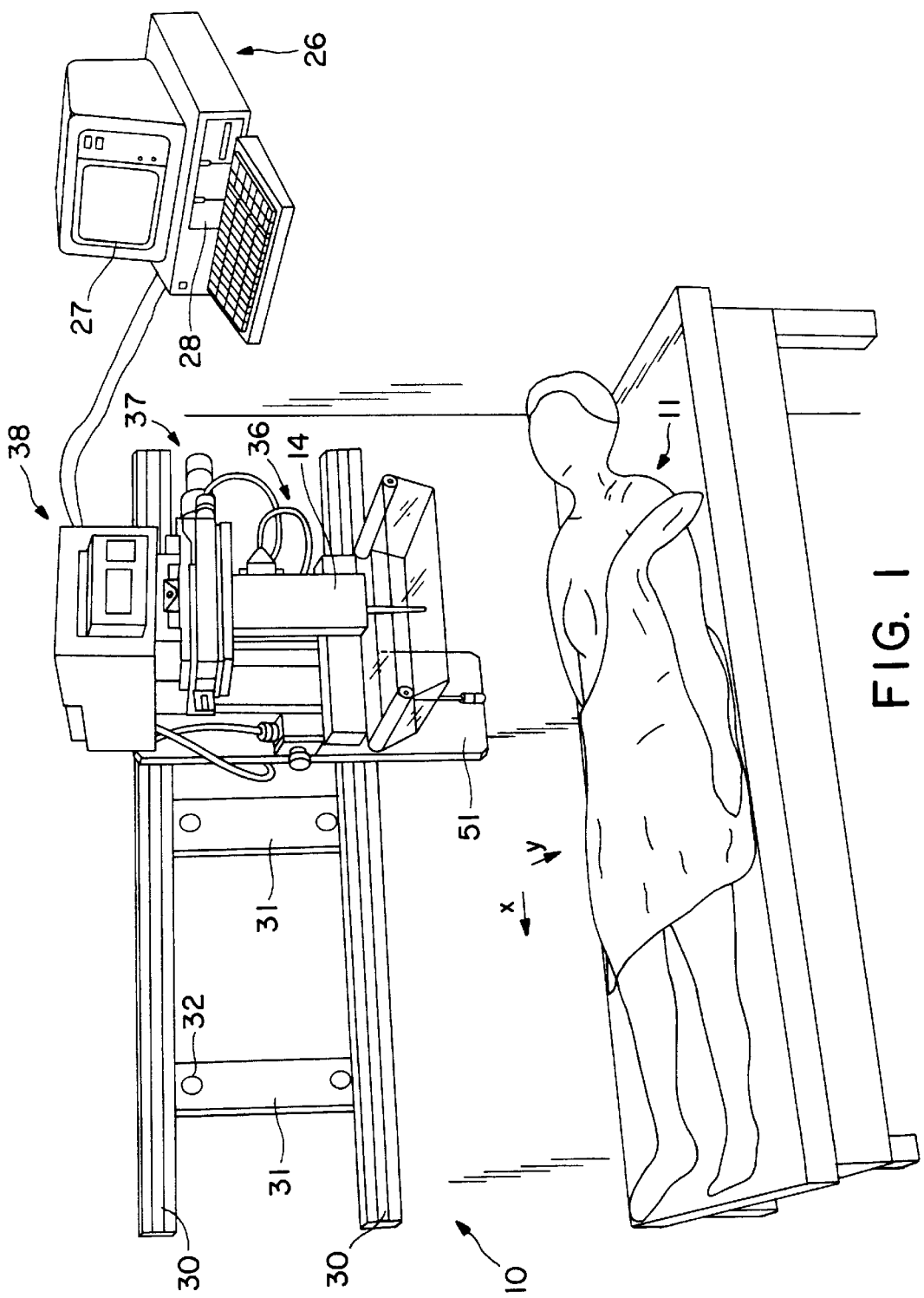
FIG. 1 is a perspective view of a tissue examination apparatus in accordance with the present invention showing a patient being prepared for examination.

It should be understood that the drawings are not necessarily to scale and that the embodiments are sometimes illustrated by graphic symbols, phantom lines, diagrammatic representations and fragmentary views. In certain instances, details that are not necessary for understanding the invention or which make other details difficult to perceive may have been omitted. It should be understood, of course, that the invention is not necessarily limited to the particular embodiments illustrated herein.

Like reference numerals will be used to refer to like parts throughout the Figures.

DETAILED DESCRIPTION OF THE INVENTION

Figure 2:
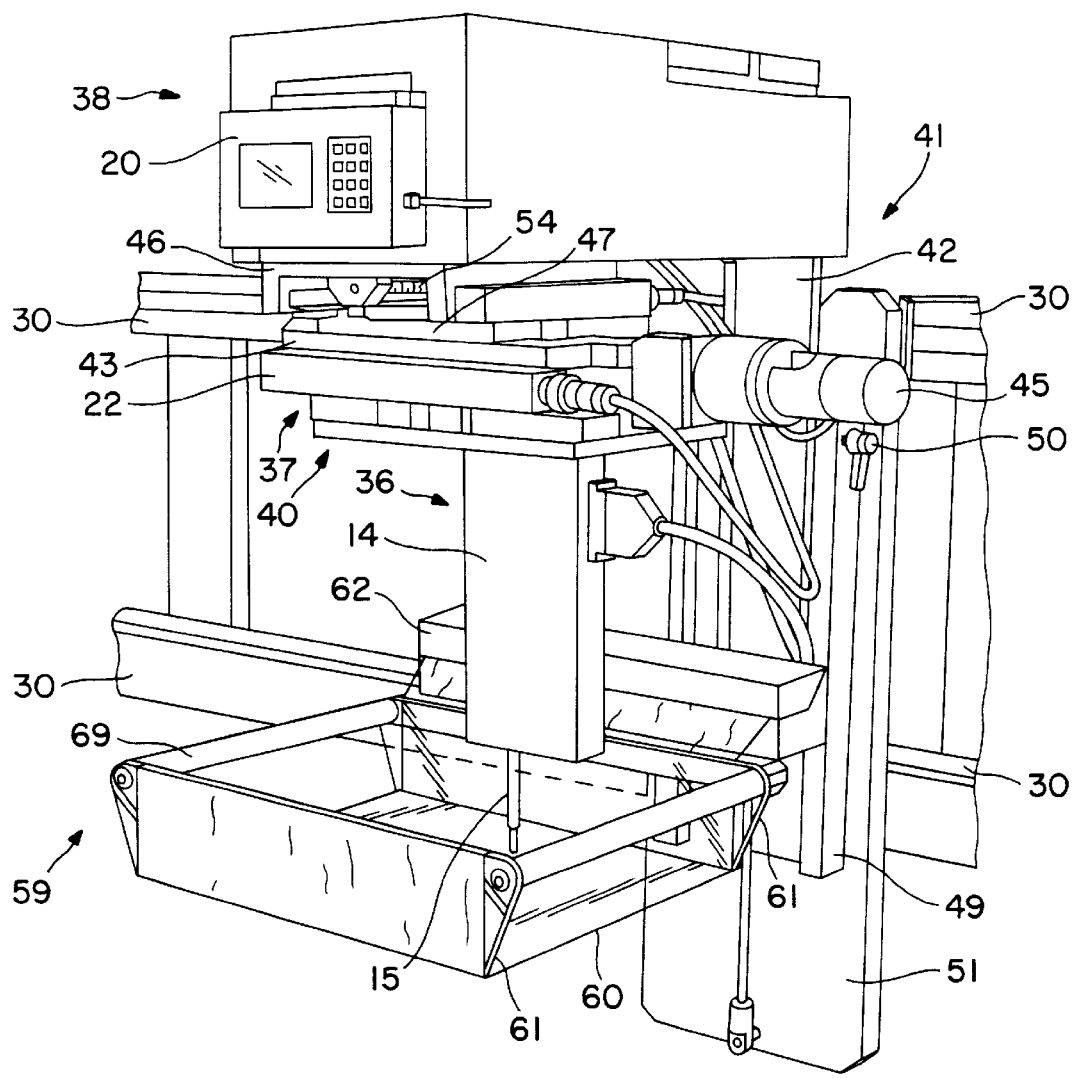
FIG. 2 is a front perspective view of the main section of the tissue examination apparatus of FIG. 1.
Figure 3:
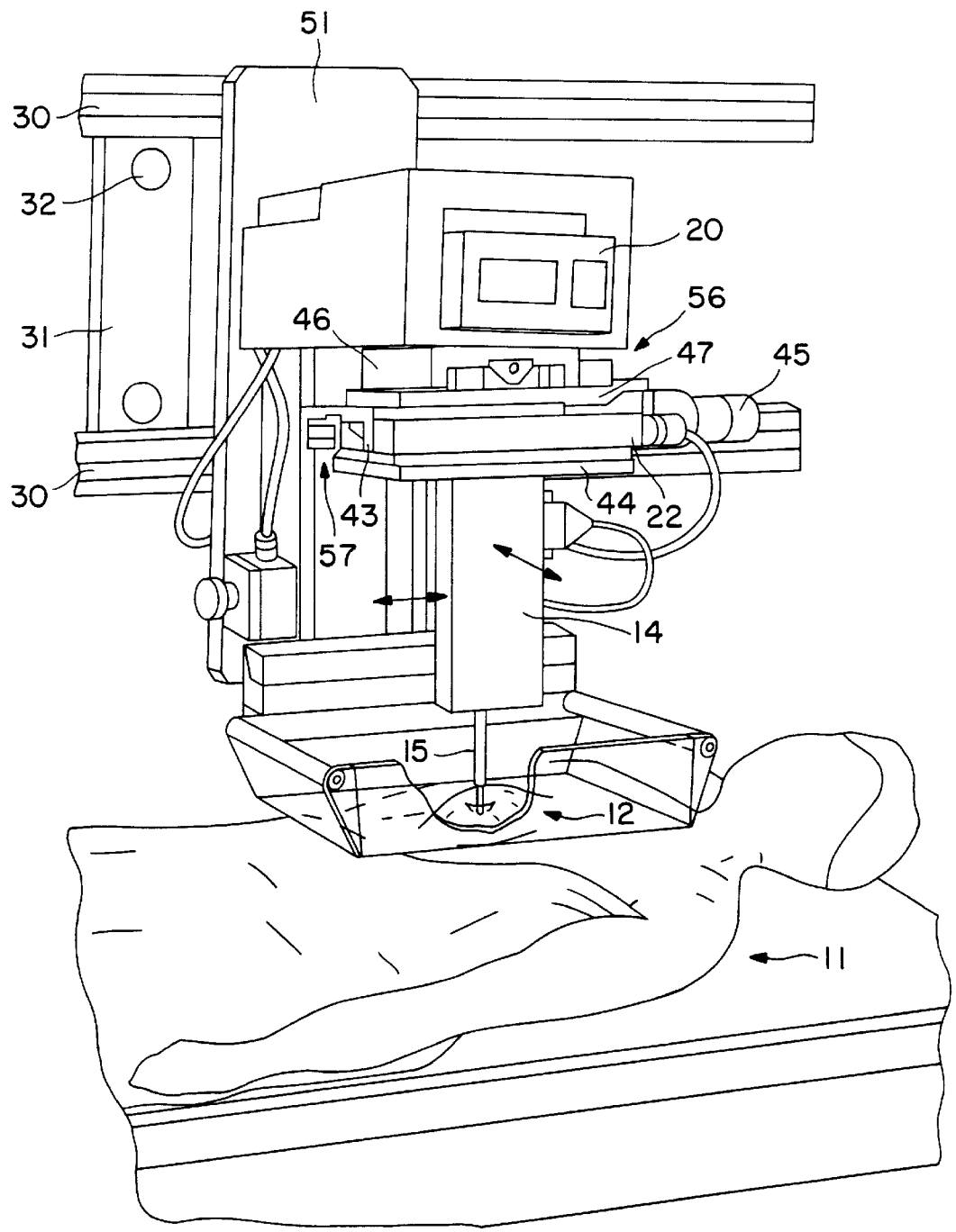
FIG. 3 is a front perspective view of the main section of the tissue examination apparatus of FIG. 1 showing the apparatus positioned over a patient for examination.

Referring now to FIGS. 1–3, there is shown a tissue examination apparatus 10 in accordance with the present invention. The apparatus 10 broadly comprises: a tissue contacting device 36; motion control components 37 for moving the tissue contacting device 36; an electronic control module 38 for controlling the tissue contacting device 36 and the motion control components 37; a support structure 41 for the tissue contacting device 36, motion control components 37 and the electronic control module 38; and a computer 26 for analyzing data generated during a tissue examination sequence.

The tissue contacting device 36 is used in the present invention in order to apply a force to tissue 12 such as a breast. In the version of the invention shown in FIGS. 1–3, the tissue-contacting device 36 is an actuator 14 including an extendable probe 15 that contacts the tissue 12 during tissue examination. The actuator 14 extends and retracts the probe 15 in response to control signals from an actuator controller (not shown). Several types of actuator systems are suitable for use in the tissue examination apparatus, such as pneumatic actuators, hydraulic actuators, mechanical actuators and electromechanical actuators. In a preferred version of the tissue examination apparatus, the actuator 14 is an electromechanical actuator and in a most preferred version of the invention, the actuator 14 is a moving coil linear servo actuator.

One moving coil linear servo actuator that may be used in the tissue examination apparatus is a Model LA-37 moving coil linear servo actuator available from SMAC, Carlsbad, Calif., USA. This actuator includes a linear moving coil that is driven electromechanically. Within the actuator body, there is a moving piston, integrating the coil, an optical encoder and the actuator probe. The piston is directly mounted onto a precision linear guide. The probe extends outward from the actuator body and has a stroke of up to 50 millimeters with a 1 micron resolution. Preferably, the probe has a ³⁄₁₆" hemispherical tip and includes a force sensor.

Many other types of sensors can be integrated with the probe tip in addition to a force sensor including: shear or other tactile or tactile array sensors; ultrasonic (higher frequency mechanical impedance measurement) sensors; capacitive sensors; inductive sensors; resistive (electrical impedance measurement) sensors; temperature sensors; or moment (3d torque) sensors. The probe may move from 0.005 mm./sec. to 1000 mm./sec. and the probe force may range from 0.1 to 9 newtons. The probe moves by direct servo motion and the position, force and speed of the probe are all fully programmable when used with a controller or other electronic control module. The actuator also provides feedback on current position and force and therefore, may be used to measure the displacement and force when the probe contacts tissue.

Because the position, force and speed of the probe are all fully programmable and the actuator can sense displacement and force, any number of probe control programs may be developed for use with the tissue contacting device. Three specific probe control controls have been found to be highly advantageous.

In a first probe control program, the probe is extended at constant velocity until a predetermined force level is encountered. When the predetermined force level is encountered, the probe control is switched to force mode, and a fixed force level is exerted for a fixed amount of time. After the fixed amount of time has elapsed, the extension of the probe is recorded, and the force level is increased to a higher fixed level. After a second fixed amount of time, the extension of the probe at this higher second level of force is recorded. After the probe is retracted, two probe extensions corresponding to the low and high force level measurements are available for data analysis.

In a second probe control program, the probe is extended at constant velocity while monitoring the position of the probe. When the probe reaches a position corresponding to a first force level, the current position is sensed, and the probe continues to extend until a position corresponding to a second force level is reached. At the second force level, the new position of the probe is then sensed. After the second force level (or near maximum extension condition) is encountered, the probe returns to its home (retracted) position.

In a third probe control program, the force and displacement of the probe are continuously measured as a function of time, and a polynomial fit to the force/displacement data. The polynomial at each X-Y grid position can then be used to evaluate the displacement corresponding to various force levels.

In the version of the invention shown, the actuator 14 is controlled by the actuator controller. One suitable actuator controller is a Model No. LAC-1 Servo Controller available from SMAC, Carlsbad, Calif., USA. This controller provides programmable control of position, speed, acceleration and force when interfaced with the moving coil linear servo actuator. This type of controller may be programmed via a "dumb terminal" or a personal computer. Preferably, this controller is set so that the forces exerted on the probe are determined by way of calculations using proportional servo tracking error.

Movement of the actuator 14 is achieved through use of the motion control components 37. Specifically, the actuator 14 is mounted on a drive assembly 40 that moves the actuator 14 in a horizontal plane over a patient 11, i.e., in the X and Y directions as shown in FIG. 1. The drive assembly 40 is constructed from a pair of ball bearing slide assemblies that are used to provide motion towards patient's feet or head (X) and towards patient's left or right (Y). The drive assembly 40 includes an upper slide assembly 56 and a lower slide assembly 57. The upper slide assembly 56 includes a slide 46, a carriage 47, a lead screw 54 and a drive motor 48. The lower slide assembly 57 also includes a slide 43, a carriage 44, a lead screw 53 and a drive motor 45. The slide 43 of the lower slide assembly 57 is mounted on the carriage 47 of the upper slide assembly 56. In this arrangement, the lower slide assembly 57 may be moved perpendicularly to the upper slide assembly 56 by movement of the carriage 47 of the upper slide assembly 56. The actuator 14 is mounted on the carriage 44 of the lower slide assembly 57. The drive motors 45, 48 of the upper slide assembly 56 and the lower slide assembly 57 may be controlled by a computer program or a programmable controller, and as the drive motors 45, 48 are energized, the corresponding lead screw rotates and the corresponding carriage travels along the lead screw. The lower slide assembly 57 and the upper slide assembly 56 are also equipped with optical home and limit sensors. The optical rotary encoders are used as a double check on the motion of the carriages 44,47 of the slide assemblies 56, 57. If the encoder, shown at 22, measures a count not consistent with the commanded steps, then interference or an abnormal operating condition can be detected. It can be appreciated that more than one actuator 14 may be mounted on the carriage 44 of the lower slide assembly 57. In this multi-actuator arrangement, the tissue examination cycle time would be shortened as a number of actuators would be available for data collection.

Suitable slide assemblies are available from Empire Automation, Woburn, Mass., USA. In the version of the tissue examination apparatus shown in FIGS. 1–3, available motion in the X-direction is 6 inches with a 200 step per revolution stepper drive motor with a 2000 count per revolution optical encoder, driving a 5 millimeter per rotation lead screw. Motion in the Y-direction is 4 inches with same motor, screw, encoder combination as in X-motion.

Coordinated motion of the actuator 14 and the upper and lower slide assemblies 56, 57 is controlled by the electronic control module 38. The electronic control module 38 in the version of the invention shown in FIGS. 1–3 includes a main controller 20 and the actuator controller described above. One suitable main controller 20 is a Model No. PK2240 controller which is available from Z-World, Davis, Calif., USA. This controller includes a fixed set of 16 protected digital inputs, 14 high-current digital outputs, 2 serial ports, and a built-in LCD and keypad for creating a custom user interface. This type of controller is suitable for connecting to a wide variety of on/off sensors, relays, actuators, or other peripheral devices. Software for this controller may be developed using Dynamic C software development system.

The main controller 20 controls and monitors motion of the drive motors 45,48 of the slide assemblies 56,57 by sending motion control signals to the drive motors 45,48 and receiving motion control signals from the drive motors 45,48. The main controller 20 also sends motion control signals to the actuator controller to initiate a probe control sequence such as one of the probe control programs described above. The main controller 20 also receives probe result data from the actuator controller and interrogates the actuator controller to verify that the probe 15 is in the home (retracted) position prior to X-Y motion.

The main controller 20 is also interfaced with the computer 26 or other similar signal processor. The computer 26 receives probe result data from the main controller 20 and is used to process, analyze and store data. The raw data and the results of the analysis may be stored in a storage device 28 of the computer 26 and may be displayed on a display device 27 of the computer. A standard 350 MHz computer may be used to store and process the data. A RS232 interface on the main controller is connected using a modular cable to the COMI RS232 port on the computer. Software such as a generic shareware "terminal" program may be used in "capture text" mode to accept and store data sent to the computer over the RS232 communications link to text files on the computer. Numeric computation and graphics software may then be used to process and display the data on the display device and/or a standard color inkjet printer.

The tissue contacting device 36, motion control components 37, and electronic control module 38 are mounted on the support structure 41 for installation in an examination room. The support structure 41 includes a pair of slides 30 that are used to provide the apparatus with horizontal travel to position the apparatus over the patient 11 and to remove the apparatus from the proximity of the patient 11 when the exam is completed. The two slides 30 are mounted to a wall in parallel spaced relationship using mounting brackets 31 that have suitable fasteners 32 for attachment to the wall. A vertical plate 51 is mounted on the slides 30 for horizontal movement relative to the slides 30. The vertical plate may be locked into position during examination by way of a self releasing electromagnet that is controlled by signals from the main controller 20. A vertical slide 49 is mounted on the front of the vertical plate 51, and L-shaped brackets 42 are mounted to the front of the vertical slide 49. The L-shaped brackets 42 form a frame to which the tissue contacting device 36, motion control components 37, and the electronic control module 38 are mounted. The L-shaped brackets 42 move up and down relative to the vertical slide 49 and may be locked into position by a manual lock down 50. The combination of the vertical slide 49 and the L-shaped brackets 42 enables the apparatus to be moved vertically up and out of the way of the patient 11 when examination is complete. Optionally, a nitrogen gas filled counterbalance cylinder may used to offset the weight of the machine to allow for easier vertical positioning.

It has been discovered that it is important to fixture tissue, such as a breast, for examination with the tissue examination apparatus 10. Therefore, a tissue stabilization device 59 is also included in the tissue examination apparatus 10. The tissue stabilization device 59 includes a pair of side plates 61, a material holder 62, and a sheet of material 60. The side plates are arranged in parallel spaced relation by way of fasteners and spacers 69. The side plates 61 of the tissue stabilization device 59 rest against the chest wall or other similar body part and the sheet of material 60 spans between the side plates 61. The sheet of material 60 contacts the tissue being examined and serves to: (1) compress the tissue (e.g., the breast), (2) immobilize the tissue, (3) aid in positioning the tissue, (4) act as a sterile barrier, and (5) provide a record of the exam. In the version of the invention shown, the tissue stabilization device 59 is integral with the tissue examination apparatus 10. However, it is possible to alternatively attach a sheet of material to the patient (e.g., tube top), or to the examination table. The sheet of material may be manufactured from any number of materials such as consumer grade commodity plastic film, thin rubber sheet (e.g., latex), synthetic mesh (e.g., pantyhose), or any of a great number of commercial film or membrane type products. Preferably, the sheet of material is a transparent commercial plastic film such as saran wrap.

Optionally, the tissue examination apparatus 10 may include a targeting device such as a laser or other pointing device (shown at 64 in FIG. 6) to allow the positioning of the machine to be repeatable with respect to the patient. For example, once a particular point on the breast is pointed to with the pointing device, e.g. nipple, that particular point can be used as a landmark to aid in visual interpretation of images generated, to aid in alignment of a time series of images for diagnostic purposes, and to aid in placement of the images obtained into the larger framework of a body image.

Having detailed the components of the tissue examination apparatus, use of the apparatus as an automated breast palpation device will be described in order to further illustrate the invention. As an initial step, the user resets the apparatus so as to return the actuator 14, the upper slide assembly 56 and the lower slide assembly 57 to their home position. The patient 11 then lies flat on an examination table and the user proceeds to properly position the tissue examination apparatus 10 over the patient as follows. First, the tissue examination apparatus 10 is moved horizontally on the pair of wall mounted slides 30 to position the apparatus over the patient 11. Second, the tissue examination apparatus 10 is lowered over the patient by way of the vertical slide 49 such that the side plates 61 of the tissue stabilization device 59 rest against the chest wall and the sheet of material 60 contacts the breasts being examined so as to compress and immobilize the breast tissue. The vertical slide 49 is then locked into position by the manual lock down 50. This arrangement of the tissue examination apparatus 10 over the patient 11 can be seen in FIG. 3.

The user then initiates a data acquisition sequence of the tissue examination apparatus 10 by pressing keys on the keypad of the main controller 20. In the data acquisition sequence, the actuator 14 is moved in the X and Y directions shown in FIG. 1 by way of the upper slide assembly 56 and the lower slide assembly 57, and the probe is extended in order to acquire readings on the tissue being examined. In one data acquisition sequence, the probe acquires readings at data acquisition points arranged in a grid pattern on the tissue being examined. Specifically, the actuator 14 is moved in a serpentine pattern by way of the upper slide assembly 56 and the lower slide assembly 57. In other words, the actuator 14 is moved from its home position in sequential positive steps in the X direction in FIG. 1 until the end of the X range is reached, then a single positive step in the Y direction is made. Sequential negative steps are made in the X direction until the beginning of the X range is reached, then a single positive Y step is made. Thus X cycles back and forth, with Y stepping once each time X reaches each extreme of its travel.

Figure 5:
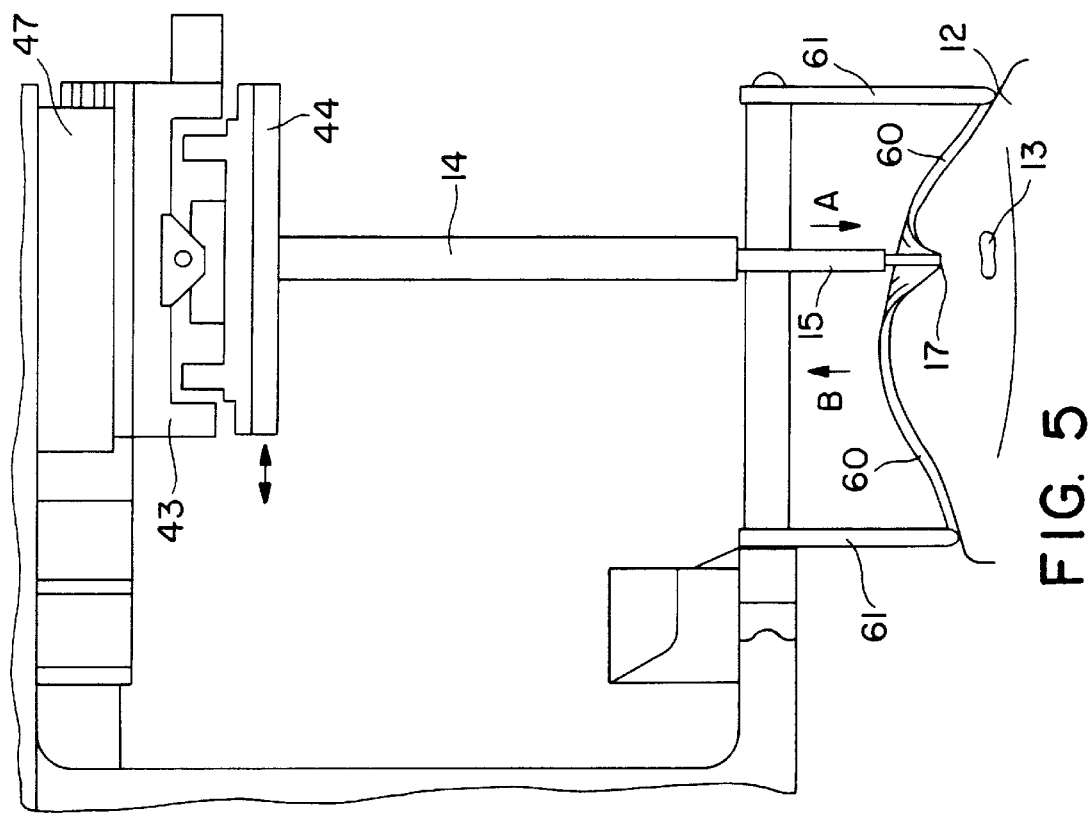
FIG. 5 is a side view of the tissue examination apparatus showing the apparatus probe at a second data acquisition position.
Figure 4:
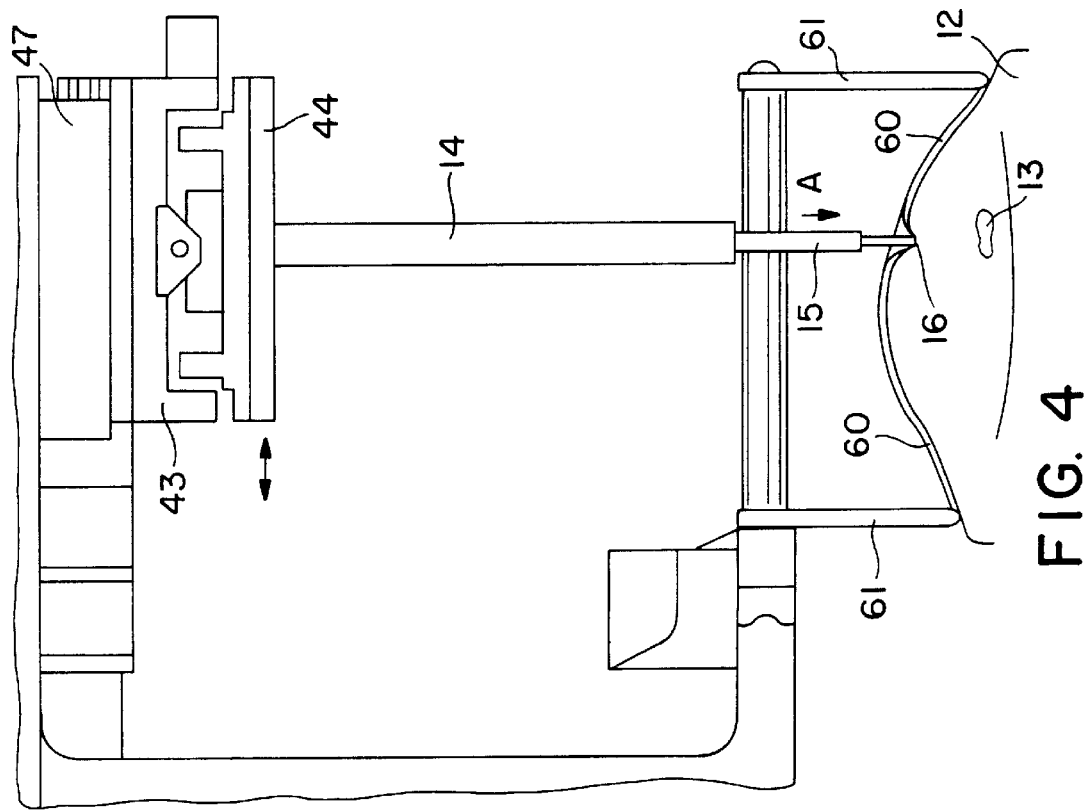
FIG. 4 is a side view of the tissue examination apparatus showing the apparatus probe at a first data acquisition position.
Figure 6:
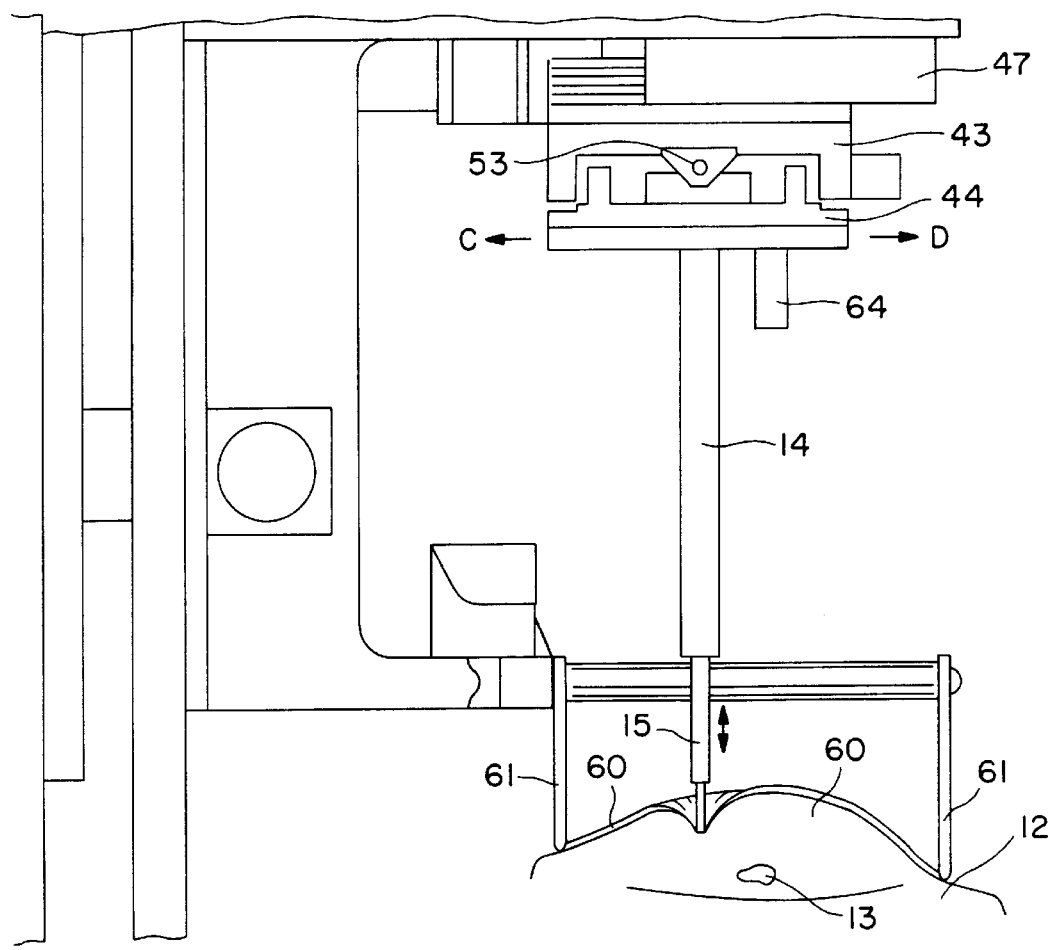
FIG. 6 is a side view of the tissue examination apparatus showing the apparatus probe at a third data acquisition position.

After each step has been made, the main controller 20 signals the actuator controller to begin extension of the probe 15. The preferred probe sequence is the second probe control program described above. In this program, the probe is extended at constant velocity while monitoring the position of the probe. When the probe contacts the breast tissue and reaches a position corresponding to a first force level, the current position is sensed, and the probe continues to extend until a position corresponding to a second force level is reached. At the second force level, the new position of the probe is then sensed. After the second force level (or near maximum extension condition) is encountered, the probe returns to its home (retracted) position. This probe sequence is shown in FIGS. 4 and 5. In FIG. 4, the probe 15 of the actuator 14 has been extended in direction 'A' into the breast tissue 12 until a first predetermined force has been reached. When the probe 15 senses this first force, the displacement of the probe at position 16 is sensed. The probe 15 is then extended further in direction 'A' into the breast tissue 12 until a second predetermined force has been reached as shown in FIG. 5. When the probe 15 senses this second force, the displacement of the probe at position 17 in FIG. 5 is sensed. The probe 15 is then retracted in direction 'B' as shown in FIG. 5. The actuator 14 is then stepped to a new location and the probe sequence is initiated again. Referring to FIG. 6, it can be seen that the probe 15 has been extended in the breast tissue 12 at a different location than FIGS. 4 and 5.

During this data acquisition sequence, the actuator controller receives displacement data from the actuator 14, and the main controller 20 receives the same data from the actuator controller. This displacement data is combined in the main controller 20 with the X and Y position data and the predetermined force data already in the memory of the main controller 20 to generate a data matrix. Specifically, the data acquisition sequence returns palpation data in the form $[X\ Y\ F_1\ F_2\ D_1\ D_2]$ where X is the X position at each data acquisition location in the grid pattern, Y is the Y position at each data acquisition location in the grid pattern, $F_1$ is the first predetermined force, $F_2$ is the second predetermined force, $D_1$ is the probe displacement at the first predetermined force, and $D_2$ is the probe displacement at the second predetermined force. The palpation data in the main controller 20 is then sent to the computer 26 over the RS232 communications link to text files on the computer 26. A numeric computation and graphics software package is then used to process and display the data on the display device and a standard color inkjet printer. Numerous software packages would be suitable for data analysis; however, a numeric computation and graphics software package called MATLAB has proven to be advantageous when used with the present invention. MATLAB is available from The MathWorks, Inc., Natick, Mass., USA.

Figure 8:
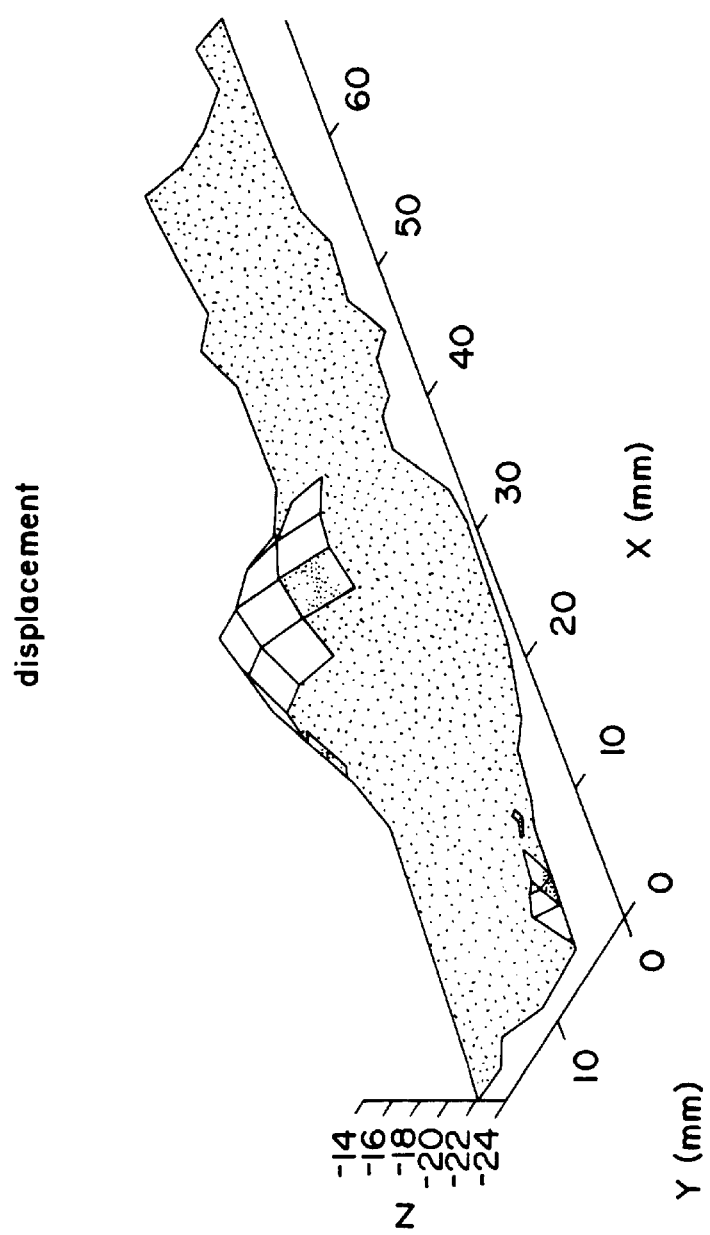
FIG. 8 shows another example of a data plot produced by the tissue examination apparatus, the plot being advantageous for diagnosis of a tissue lesion.
Figure 9:
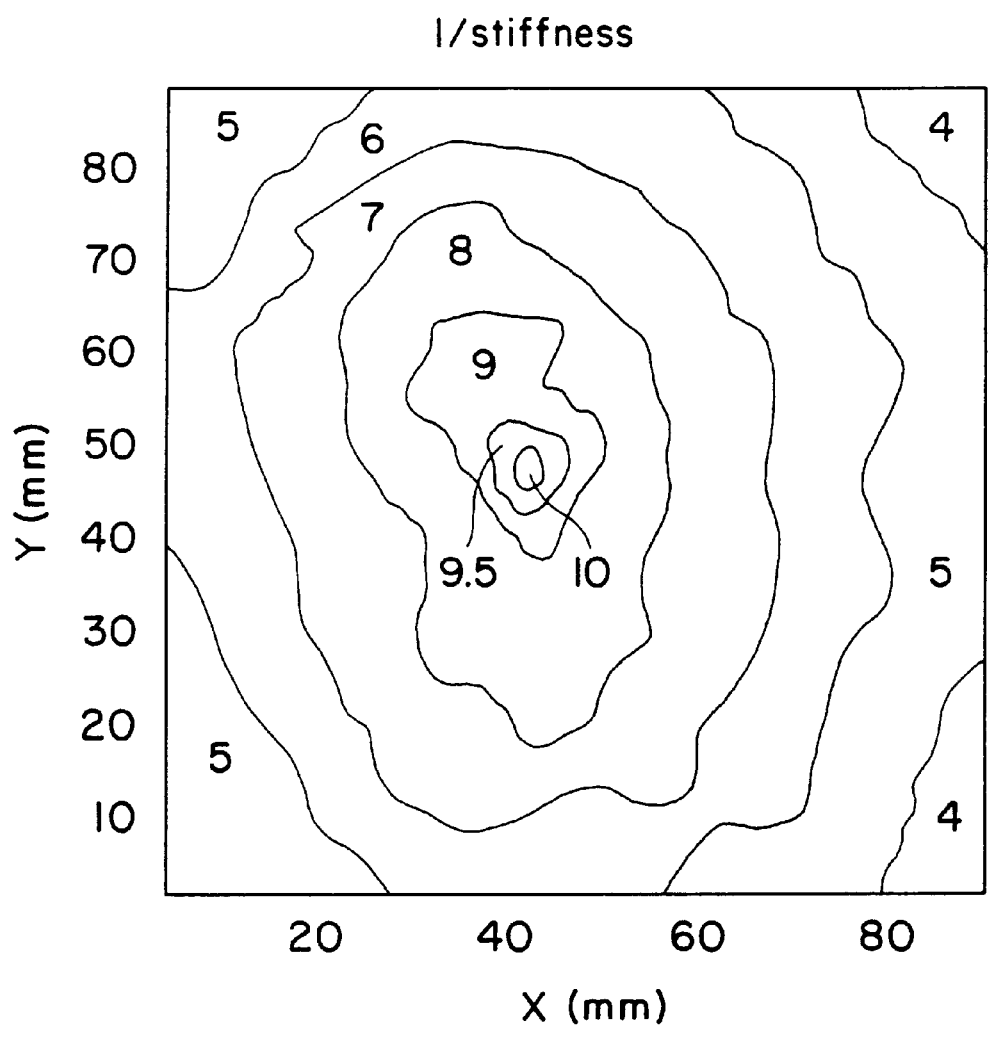
FIG. 9 shows yet another example of a data plot produced by the tissue examination apparatus, the plot being advantageous for diagnosis of a tissue lesion.

The numeric computation and graphics software package is used to generate two or three dimensional plots, with a single line tracing out the serpentine X-Y data acquisition pattern. These plots are displayed on the display device 27 or printer in order to assist in diagnosis of a lesion or tumor. In the one of the plots, X and Y plot coordinates correspond to the X-Y locations of the probe, and the Z dimension corresponds to the probe displacement $D_1$ or $D_2$. The numeric computation and graphics software package is also used to sort the data $[X\ Y\ F_1\ F_2\ D_1\ D_2]$ into a matrix format, for further three dimensional plotting. Surface and contour plots are generated using the X-Y probe locations for X-Y positions on the plots, Z probe displacement for Z displacement on the plots, and a color scheme based on several alternative schemes. Color can be simply based on displacement, thus all points of the surface at a fixed height are of the same color. Alternatively, other parameters can be used as the basis of the color scheme. For example, the color can be based on the difference in displacement at a given X-Y location, for the two different force levels (measure of inverse stiffness), alternatively the rate of change of Z displacement with respect to the X and/or Y directions can be used as a measure of the slope or gradient of the surface. As a further alternative, the data can be displayed as contour plots instead of surface plots. Examples of plots used in diagnosis are shown in FIGS. 7–9.

Figure 7:
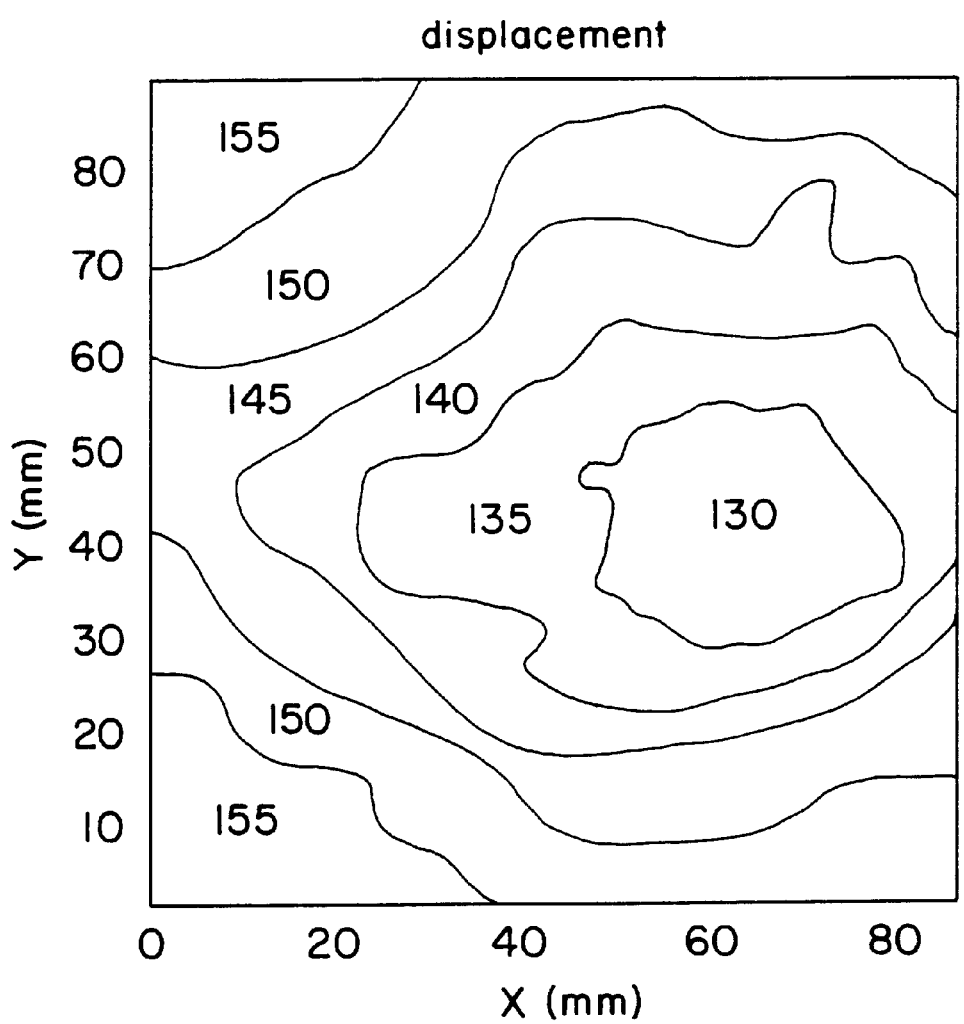
FIG. 7 shows one example of a data plot produced by the tissue examination apparatus, the plot being advantageous for diagnosis of a tissue lesion.

Examining FIG. 7 in more detail, it can be seen that this two dimensional plot allows the viewer to easily interpret the data acquired when the tissue examination apparatus is used as an automated breast palpation device. In this plot, the X and Y position grid are shown on the X and Y axes respectively. The home position of the upper and lower slide assemblies corresponds to the '0' point on the X and Y axes. In this data acquisition sequence, the actuator 14 has been moved in 5 millimeter steps in a serpentine pattern over an 80 millimeter by 80 millimeter grid by way of the upper slide assembly 56 and the lower slide assembly 57. At each step of the slide assemblies, the probe is extended to contact the breast tissue until the probe reaches a position corresponding to a first force level and then the current position is sensed. The probe continues to extend until a position corresponding to a second force level is reached. At the second force level, the new position of the probe is then sensed. After the second force level (or near maximum extension condition) is encountered, the probe returns to its home (retracted) position.

In FIG. 7, the plot shows displacement ranges for a predetermined force level $F_1$. Looking more closely at FIG. 7, it can be seen that at the grid position X=60 mm and Y=40 mm, the displacement was approximately 130, while at the grid position X=20 mm and Y=10 mm, the displacement was approximately 155. These areas of different displacement can be shown using a color scheme on a display device or color printer.

The plot of FIG. 7 may be interpreted as follows. Typically, the tissue in a breast will have a generally uniform stiffness and therefore, the displacement at a predetermined force should be approximately uniform within the grid of tissue examination. However, should the tissue contain a lump, such as the lump 13 shown in FIGS. 4–6, a predetermined force will be reached at a lower displacement as the stiff lump provides resistance to motion of the actuator probe. By comparing displacement readings within the grid of FIG. 7, it can be seen that areas with a lower displacement (i.e., 130) are surrounded by areas with increasing displacement (i.e., 135, 140, 145, 150, 155). This indicates that an area of stiffer tissue is located near the grid position X=60 mm and Y=40 mm.

FIG. 8 shows an example of a three dimensional plot that provides even further indication of a localized region of stiffer tissue within surrounding tissue. In this plot, the X and Y position grid are shown on the X and Y axes respectively and the displacement distance is plotted on the Z axis. This type of plot shows the general shape of the lump by plotting displacement distance at each grid point. Grid points having the lowest displacement appear at the upper regions of the plot and grid points having the highest displacement appear at the lower regions of the plot. In this manner it is possible to generally outline the shape of a region of stiffer tissue (i.e., a lump).

FIG. 9 shows a stiffness plot that also indicates regions of higher stiffness. A stiffness plot is developed using two force and two displacement readings; therefore, probe control programs that measure displacement at two different locations are necessary for this plot. Interpretation of FIG. 9 is similar to that of FIG. 7.

In another version of the invention, the probe tip is fitted with a roller to perform line scans in various directions. The actuator is replaced by an actuator that also allows for rotation of the probe. The roller can rotate about the vertical axis to allow both X and Y line scans and continuous force and displacement measurements. A power roller can also be used to reduce side load and ease travel. One suitable actuator for this version of the invention is a Model RLA-37 moving coil linear servo actuator available from SMAC, Carlsbad, Calif., USA. In yet another version of the invention, the actuator and probe can be reprogrammed to also measure mass and damping properties of the tissue.

Therefore, it can be seen that the tissue examination apparatus of the present invention provides numerous improvements over manual breast palpation techniques. For instance, the tissue examination apparatus:

(1) uses an actuator and probe system that can measure tissue resistance with far greater accuracy than human fingers;

(2) uses electronic controllers and signal processors that can convert probe measurements into visual images that can be displayed and printed for retention;

(3) allows breast palpation to be used in serial studies as data files and data images can be saved for comparison to the results of a subsequent examination;

(4) can be installed at a mammography facility so that a mammogram and an automated breast palpation examination can be completed in one appointment;

(5) includes systems that allow for a reproducible physical examination;

(6) includes signal processors, such as a computer, that can be used to both enhance the data to make visual inspection of images easier and that can perform automated evaluation of the data to flag or otherwise highlight suspect tissue areas;

(7) creates objective data that can be combined with objective data from automated mammographic or other exams for improved predictive value; and (8) analyzes palpation data and creates displacement maps, stiffness maps, curvature maps, gradient maps, and corresponding contour maps that can be compared to maps created taken at different points in time to detect changes.

Although the invention has been described in considerable detail with reference to certain preferred embodiments, one skilled in the art will appreciate that the present invention can be practiced by other than the preferred embodiments, which have been presented for the purpose of illustration and not of limitation. Therefore, the spirit and scope of the appended claims should not be limited to the description of the preferred embodiments illustrated herein.

What is claimed is:

1. A tissue examination apparatus for performing an examination of breast tissue of a person with a breast facing upwardly comprising:

an actuator having a downwardly extendable probe for contacting tissue;

an electronic control module communicating with the actuator, the electronic control module controlling extension and retraction of the probe, and the electronic control module determining displacement distances of the probe and forces exerted on the probe at each displacement distance when the probe is extended so as to contact the tissue; and a signal processor communicating with the electronic control module and receiving the force and the displacement distance determinations from the electronic control module, the signal processor analyzing the force and the displacement distance determinations to provide a data analysis indicating any localized area of stiffer or softer tissue within the tissue, a support structure, a sheet of material secured to a support structure and adapted to be placed over and in contact with said breast facing upwardly, the sheet of material immobilizing the tissue being examined.

2. The tissue examination apparatus of claim 1 further comprising:

the actuator and the electronic control module being mounted on the support structure.

3. The tissue examination apparatus of claim 2 wherein:

the support structure includes a frame and a motion control assembly, the motion control assembly including a movable carriage, the motion control assembly being mounted on the frame, and the actuator being mounted on the movable carriage.

4. The tissue examination apparatus of claim 3 wherein:

the motion control assembly further includes a drive motor for moving the carriage, the drive motor receiving motion control signals from the electronic control module.

5. The tissue examination apparatus of claim 1 further comprising:

a targeting device mounted on the support structure, the targeting device enabling placement of the support structure in a particular spatial relationship with a predetermined area of tissue.

6. The tissue examination apparatus of claim 1 further comprising:

a storage device communicating with the signal processor, the storage device storing the force and the displacement determinations and the data analysis of the signal processor in order to allow a user to perform serial data analysis.

7. The tissue examination apparatus of claim 1 further comprising:

a display device communicating with the signal processor, the display device displaying the data analysis of the signal processor.

8. The tissue examination apparatus of claim 1 wherein:

the probe has a tissue-engaging tip including at least one sensor selected from the group consisting of force sensors, shear or other tactile or tactile array sensors, ultrasonic sensors, capacitive sensors, inductive sensors, resistive sensors, temperature sensors, and moment sensors.

9. A tissue examination apparatus comprising:

an actuator having an extendable probe for contacting tissue;

an electronic control module communicating with the actuator, the electronic control module controlling extension and retraction of the probe, and the electronic control module determining displacement distances of the probe and forces exerted on the probe at each displacement distance when the probe is extended so as to contact the tissue; and a signal processor communicating with the electronic control module and receiving the force and the displacement distance determinations from the electronic control module, the signal processor analyzing the force and the displacement distance determinations to provide a data analysis indicating any localized area of stiffer or softer tissue within the tissue a support structure, the actuator and the electronic control module being mounted on the support structure the support structure includes a frame and a pair of motion control assemblies secured to the frame, each motion control assembly including a movable carriage and a corresponding drive motor, each drive motor receiving motion control signals from the electronic control module, the motion control assemblies being mounted on the frame, and the actuator being mounted on one of the movable carriages.

10. The tissue examination apparatus of claim 9 wherein:

the electronic control module transmits signals to the actuator and the drive motors such that the actuator moves in a predetermined pattern over the tissue and the probe extends and retracts in a predetermined sequence.

11. An apparatus for the detection and monitoring of lesions in a human breast, the apparatus comprising:

an actuator having an extendable probe for contacting the breast;

an electronic control module communicating with the actuator, the electronic control module controlling extension and retraction of the probe, and the electronic control module determining displacement distances of the probe and forces exerted on the probe at each displacement distance when the probe is extended so as to contact the breast;

a frame;

a pair of motion control assemblies secured to the frame, each motion control assembly including a movable carriage and a corresponding drive motor, each drive motor receiving motion control signals from the electronic control module, the motion control assemblies being mounted on the frame, and the actuator being mounted on one of the movable carriages;

a sheet of material secured to the frame, the sheet of material immobilizing the breast being examined; and a signal processor communicating with the electronic control module and receiving the force and the displacement distance determinations from the electronic control module, the signal processor analyzing the force and the displacement distance determinations to provide a data analysis indicating any lesion within the breast.

12. The apparatus of claim 11 wherein:

the electronic control module transmits signals to the actuator and the drive motors such that the actuator moves in a predetermined pattern over the breast and the probe extends and retracts in a predetermined sequence.

13. The apparatus of claim 12 further comprising:

a display device communicating with the signal processor, the display device displaying the data analysis of the signal processor.

14. The apparatus of claim 13 further comprising:

a storage device communicating with the signal processor, the storage device storing the force and the displacement determinations and the data analysis of the signal processor.

15. The apparatus of claim 14 further comprising:

a pair of opposed spaced apart panels mounted on the frame, the panels being adjustable so that the panels may be positioned on opposite sides of the rib cage of a patient being examined.

16. The apparatus of claim 15 further comprising:

a targeting device mounted on the frame, the targeting device enabling placement of the frame in a particular spatial relationship with a predetermined area of the breast.

17. The apparatus of claim 15 wherein:

the probe has a tissue-engaging tip including at least one sensor selected from the group consisting of force sensors, shear or other tactile or tactile array sensors, ultrasonic sensors, capacitive sensors, inductive sensors, resistive sensors, temperature sensors, and moment sensors.

18. The apparatus of claim 15 wherein:

the probe has roller tip.

19. The apparatus of claim 11 wherein:

the forces exerted on the probe are determined by way of calculations using proportional servo tracking error.

20. An apparatus for the detection and monitoring of lesions in a human breast, the apparatus comprising:

a plurality of actuators, each actuator having an extendable probe for contacting the breast;

an electronic control module communicating with each actuator, the electronic control module controlling extension and retraction of each probe, and the electronic control module determining displacement distances of each probe and forces exerted on each probe at each displacement distance when each probe is extended so as to contact the breast;

a frame;

a pair of motion control assemblies secured to the frame, each motion control assembly including a movable carriage and a corresponding drive motor, each drive motor receiving motion control signals from the electronic control module, the motion control assemblies being mounted on the frame, and each actuator being mounted on one of the movable carriages;

a sheet of material secured to the frame, the sheet of material immobilizing the breast being examined; and a signal processor communicating with the electronic control module and receiving the force and the displacement distance determinations from the electronic control module, the signal processor analyzing the force and the displacement distance determinations to provide a data analysis indicating any lesion within the breast.

21. The apparatus of claim 20 wherein:

the electronic control module transmits signals to each actuator and the drive motors such that each actuator moves in a predetermined pattern over the breast and each probe extends and retracts in a predetermined sequence.

* * * * *